(12) United States Patent
Pivette et al.

(10) Patent No.: US 11,266,614 B2
(45) Date of Patent: Mar. 8, 2022

(54) ORAL FORMULATIONS OF BELINOSTAT

(71) Applicant: ONXEO, Paris (FR)

(72) Inventors: Perrine Pivette, Alfortville (FR); Caroline Lemarchand, Paris (FR); Ian Yates, Bend, OR (US); Corey Bloom, Bend, OR (US)

(73) Assignee: ONXEO, Paris (FR)

( * ) Notice: Subject to any disclaimer, the term of this patent is extended or adjusted under 35 U.S.C. 154(b) by 44 days.

(21) Appl. No.: 16/627,643

(22) PCT Filed: Jun. 29, 2018

(86) PCT No.: PCT/EP2018/067717
§ 371 (c)(1),
(2) Date: Dec. 30, 2019

(87) PCT Pub. No.: WO2019/002614
PCT Pub. Date: Jan. 3, 2019

(65) Prior Publication Data
US 2020/0155485 A1 May 21, 2020

Related U.S. Application Data

(60) Provisional application No. 62/527,684, filed on Jun. 30, 2017.

(30) Foreign Application Priority Data

Jul. 3, 2017 (EP) .................. EP17305853

(51) Int. Cl.
*A61K 31/18* (2006.01)
*A61K 9/00* (2006.01)
*A61K 31/4172* (2006.01)
*A61K 47/32* (2006.01)

(52) U.S. Cl.
CPC ............ *A61K 31/18* (2013.01); *A61K 9/0053* (2013.01); *A61K 31/4172* (2013.01); *A61K 47/32* (2013.01)

(58) Field of Classification Search
CPC ....................................................... A61K 31/18
See application file for complete search history.

(56) References Cited

U.S. PATENT DOCUMENTS

2008/0317851 A1  12/2008  Appel et al.
2014/0148449 A1  5/2014  Bi et al.
2015/0231134 A1  8/2015  Erichsen

FOREIGN PATENT DOCUMENTS

AU  2012 213 940   3/2015
WO  WO-2011064663  6/2011

OTHER PUBLICATIONS

International Search Report dated Sep. 27, 2018 in International Application No. PCT/EP2018/067717.
Written Opinion dated Sep. 27, 2018 in International Application No. PCT/EP2018/067717.
European Search Report dated Dec. 4, 2017 in European Application No. EP 17 30 5853.
Steele et al. (Cancer Chemother. Pharmacol. 2011, 67:1273-1279), "Pharmacokinetic and pharmacodynamics properties of an oral formulation of the histone deacetylase inhibitor Belinostat (PXD101)".

*Primary Examiner* — Golam M Shameem
(74) *Attorney, Agent, or Firm* — B. Aaron Schulman, Esq.; Stites & Harbison, PLLC

(57) ABSTRACT

The present application concerns new formulations of belinostat suitable for oral administration, their process of preparation, the pharmaceutical compositions comprising said formulations and their uses thereof.

11 Claims, 1 Drawing Sheet

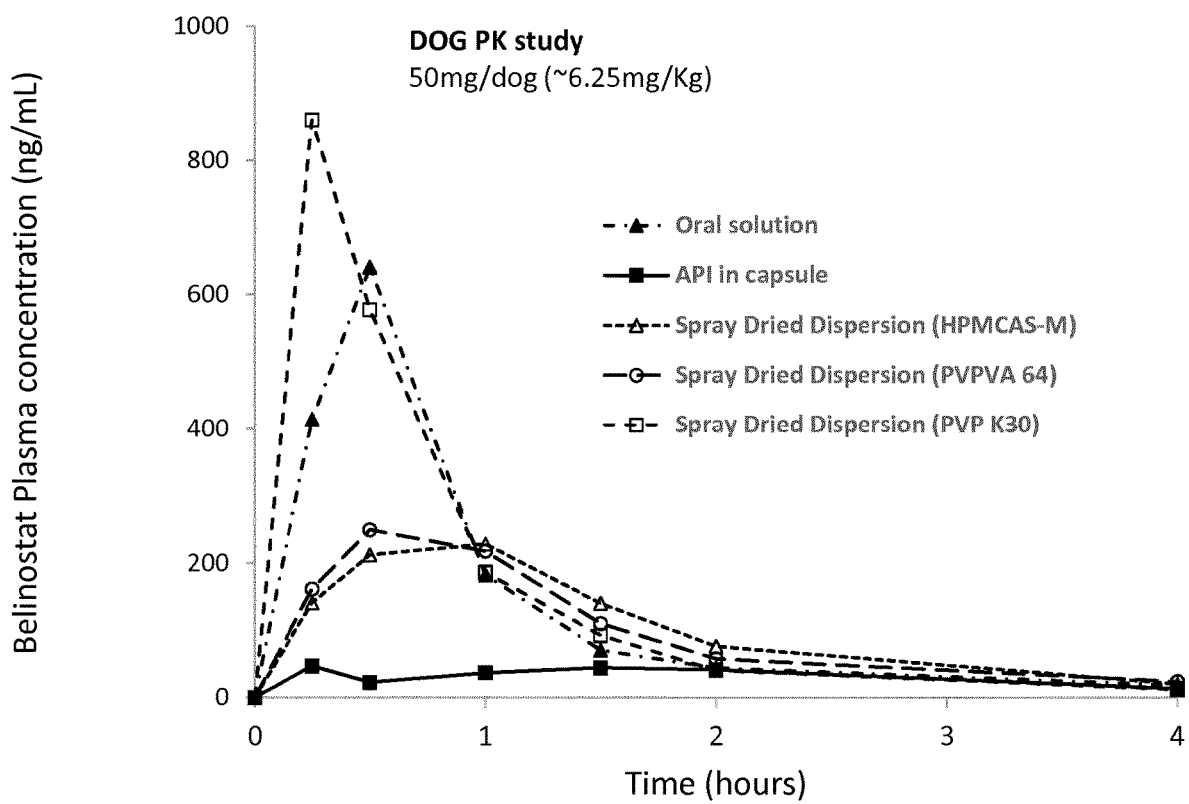

ORAL FORMULATIONS OF BELINOSTAT

The present invention concerns a new oral formulation for belinostat.

BACKGROUND OF THE INVENTION

Belinostat is a histone deacetylase inhibitor (HDAC inhibitor) with a sulfonamide-hydroxamide structure. The chemical name of belinostat is: (2E)-N-hydroxy-3-[3-(phenylsulfamoyl)phenyl]prop-2-enamide. Its structural formula is as follows:

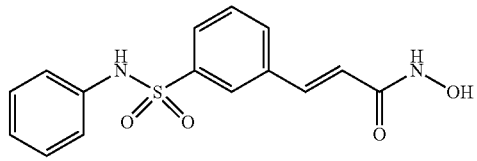 [SMILES: O=C(/C=C/c1cccc(S(=O)(=O)Nc2ccccc2)c1)NO]

Belinostat is marketed as Beleodaq®, a sterile lyophilized yellow powder for injection containing 500 mg of belinostat as the active ingredient. Each vial also contains 1000 mg L-Arginine, USP as an inactive ingredient. It is intended for intravenous administration after reconstitution with water: The powder is mixed with 9 ml of sterile water for injection and the reconstituted solution is further diluted with 250 ml of sterile 0.9% sodium chloride for injection prior to infusion. Beleodaq® is indicated for the treatment of patients with relapsed or refractory peripheral T-cell lymphoma (PTCL). Its recommended dosage is 1000 mg/m² administered over 30 minutes by intravenous infusion once daily on days 1-5 of a 21 day cycle. Cycles can be repeated every 21 days until disease progression or unacceptable toxicity.

The administration by injection is burdensome for the patients and an oral form is generally desired to facilitate patient compliance.

To allow for flexible dosing and combination regimens, an oral formulation (crystalline drug in capsules) of belinostat has been developed and tested in clinical studies. Despite showing clinical promise, the use of powder capsules of belinostat has been limited due to the variability of exposure across dose range from 250 mg to 2000 mg. Additionally, a high variability in clearance of oral belinostat was reported by Steele et al. (Cancer Chemother. Pharmacol. 2011, 67:1273-1279) who studied the pharmacokinetic and pharmacodynamic properties of belinostat administered by oral route, as a crystalline powder in capsules at high doses of oral belinostat (up to 1000 mg/m² bid for 5 consecutive days).

This can be related to the poor physicochemical properties of belinostat which presents a low solubility in water (0.14 mg/mL). Further, belinostat is also significantly metabolized (especially glucuronidation by UGT1A1 enzymes) thus also inducing potential significant variability (Wang et al., PLoS One. 2013; 8(1):e54522).

As a comparison, other clinically advanced hydroxamic acid based HDAC inhibitors were initially developed as intravenous (IV) products but they have been further developed and marketed as oral solid dosage form.

Worth noting is vorinostat:

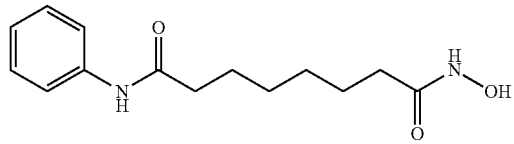 [SMILES: O=C(CCCCCCC(=O)Nc1ccccc1)NO]

Vorinostat presents poor solubility in water (0.19 mg/mL), moderate permeability and extensive first pass metabolism reported in animal and human studies. The major pathways of vorinostat metabolism involve glucuronidation and hydrolysis followed by β-oxidation. In a phase I trial, an absolute oral bioavailability of 43% was reported.

Vorinostat (Zolinza®) is marketed as 100 mg capsules containing microcrystalline cellulose, sodium croscarmellose and magnesium stearate (Vorinostat package insert).

Panobinostat lactate (Farydak®) is another hydroxamic based HDAC inhibitor:

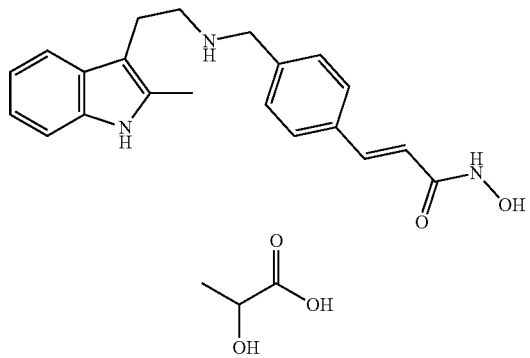

Anhydrous panobinostat lactate is slightly soluble in water. The aqueous solubility of panobinostat lactate is pH dependent, with a maximum solubility at pH 2 or 3 (~5 mg/mL), a low solubility at neutral pH (0.3 mg/mL at pH 6.8) and very low solubility at pH 7.6 (0.07 mg/mL). It is highly permeable but it is extensively metabolized through reduction, hydrolysis, oxidation, and glucuronidation processes. The absolute oral bioavailability of Farydak® is approximately 21%.

Panobinostat is marketed as 10, 15 and 20 mg capsules containing magnesium stearate, mannitol, microcrystalline cellulose and pregelatinized starch (Label Panobinostat package insert).

Despite the fact that these molecules present similar physicochemical and pharmacokinetic properties as belinostat (poor solubility, high metabolism and low to moderate oral bioavailability), they were successfully marketed for oral administration using conventional solid dosage forms such as simple powder blend in capsules.

Due to the specific variability of exposure and limited bioavailability observed for higher doses of crystalline belinostat in capsules, there is the need for a particular oral dosage form that will provide increased bioavailability and consequently increased potential therapeutic effect.

To overcome poor solubility property of belinostat which is a limiting factor for absorption, various solubilizing strategies have been attempted. Among pH modification, cosolvent system, cyclodextrin complexation, acidic or basic in situ salt and combination of these techniques, the in situ salt was adequate to achieve an increase in solubility of belinostat to a satisfactory level. However, the use of this approach is not pharmaceutically acceptable as an oral form due to the pH of the saturated solution above pH 9. In addition, poor chemical stability of belinostat in liquid solution at above pH 8.5 was reported by Finn et al, (2016), The Discovery and Development of belinostat, in Successful Drug Discovery (eds J. Fischer and W. E. Childers), Wiley-VCH Verlag GmbH & Co. KGaA, Weinheim, Germany, chapter 3. Early stage preclinical formulations using cosolvent showed enhanced exposure compared to crystalline form but they are also not pharmaceutically acceptable for repeated dosing due to high amount of cosolvent.

It is therefore very challenging to achieve an oral formulation of belinostat, which is physically and chemically stable, and also enhances the dissolution and oral bioavailability of belinostat. Yet there is a need for an effective and stable delivery system that can provide clinically viable oral administration of belinostat. Thus, it was an object of the present invention to provide compositions comprising belinostat for oral administration, which compositions have advantageous characteristics regarding solubility and/or bioavailability and/or the stability.

SUMMARY OF THE INVENTION

Surprisingly, it was found that this object can be achieved by providing a solid dispersion comprising belinostat in amorphous form and at least one non-ionizable (neutral) non-cellulosic polymer, such as a polyvinyl lactam polymer.

The challenge was to find a composition that will prevent recrystallization with time (good physical stability) and good chemical stability as molecules in amorphous state can be prone to instability during storage due to higher mobility of molecules in amorphous state. In addition to the good stability in the solid state, the composition should also improve the dissolution profile by inhibiting crystallization from the supersaturated solution generated by dissolution of the amorphous material.

As described below, it was surprisingly found that only one particular category of matrix compounds (polymers), namely the non-ionizable (neutral) non-cellulosic polymers leads to an increased solubility of belinostat, together with a satisfying physical and chemical stability, and an increased bioavailability.

DETAILED DESCRIPTION

According to a first objet, the present invention provides an amorphous solid dispersion (ASD) of belinostat comprising:

a) Belinostat or a pharmaceutically acceptable salt, solvate or ester thereof;

b) At least one non-ionizable (neutral) non-cellulosic polymer; and c) Optionally, at least one additive.

The term "solid dispersion" refers to a composition in a solid state, i.e. a state which is neither liquid nor gaseous, wherein the belinostat is dispersed in at least one pharmaceutically acceptable polymer comprised in the solid dispersion. The term "solid dispersion" as used herein encompasses all known categories of solid dispersions, i.e. simple eutectic mixtures, solid solutions, such as continuous solid solutions, discontinuous solid solutions, substitutional crystalline, interstitial crystalline and amorphous solid solutions, glass solutions and amorphous precipitations in crystalline carriers. According to the invention, the solid dispersion is an amorphous solid dispersion (ASD).

As used herein, the term "amorphous solid dispersion" (ASD) refers to a dispersion of drug in a solid polymer in an amorphous state. The term "amorphous solid dispersion" refers to solid dispersions comprising belinostat in a substantially amorphous solid form. Preferably, amorphous particles of belinostat are dispersed in the polymer. The term "substantially amorphous solid form" is intended to mean that at least 80% by weight, typically at least 85% by weight, preferably at least 90% by weight, more preferably at least 95% by weight, still more preferably at least 96% by weight, still more preferably at least 97%, more preferably at least 98% by weight, more preferably at least 99% by weight, more preferably at least 99.9% by weight, more preferably all belinostat, is present in amorphous form. ASD consists of the mixture of the drug substance with a polymer to stabilize the amorphous drug.

"Amorphous" relates to the non-crystalline state of a solid. Amorphous solids generally possess crystal-like short-range molecular arrangements, i.e. no long-range order of molecular packing found in crystalline solids. The solid state form of a solid in the solid dispersion may be determined by polarized light microscopy, X-ray powder diffraction, differential scanning calorimetry or other techniques known to those of skill in the art. The amorphous state of belinostat in the solid dispersion can be identified by a distinctive broad X-Ray powder diffraction pattern, whereas crystalline solids lead to specific isolated peaks. The amorphous state can exist in two states: one rubbery state and one glass state, where one state converts to the other one at the glass transition temperature (Tg).

Belinostat and methods for synthetizing the same are described in the international patent application WO 2002/30879. The amorphous solid dispersion may comprise any pharmaceutically acceptable form of belinostat, including without limitation, its free form and its pharmaceutically acceptable salts, solvates or esters thereof.

The term "pharmaceutically acceptable salts" refers to salts prepared from pharmaceutically acceptable, preferably non-toxic, bases or acids including mineral or organic acids or organic or inorganic bases. Such salts are also known as acid addition and base addition salts." Examples of pharmaceutically acceptable salts are discussed in Berge et al., 1977, "Pharmaceutically Acceptable Salts," J. Pharm. Sci., Vol. 66, pp. 1-19.

The term "solvate" refers to a molecular complex comprising the drug substance and a stoichiometric or non-stoichiometric amount of one or more pharmaceutically acceptable solvent molecules (e.g., ethanol). The term "hydrate" refers to a solvate comprising the drug substance and a stoichiometric or non-stoichiometric amount of water.

Alternatively, belinostat may be used in a chemically protected form. The term "chemically protected form" pertains to a compound in which one or more reactive functional groups are protected from undesirable chemical reactions, that is, are in the form of a protected or protecting group (also known as a masked or masking group). Regarding belinostat, a hydroxy group may be protected as an organic or inorganic ester, for example, an acetyl ester (—OC(=O)CH 3, —OAc) or a phosphate ester.

As used herein, the expression "non-ionizable (neutral) non-cellulosic polymers" refers to vinyl polymers and copolymers having at least one substituent selected from the group consisting of hydroxyl, alkylacyloxy, and cyclicamido; polyvinyl alcohols that have at least a portion of their repeat units in the unhydrolyzed (vinyl acetate) form;

polyvinyl alcohol polyvinyl acetate copolymers; polyvinyl pyrrolidone; polyoxyethylene-polyoxypropylene copolymers, also known as poloxamers; and polyethylene polyvinyl alcohol copolymers.

According to an embodiment, "non-ionizable (neutral) non-cellulosic polymers" do not include non-ionizable (neutral) cellulosic polymers, such as hydroxypropyl methyl cellulose acetate, hydroxypropyl methyl cellulose (HPMC) also referred as hypromellose, hydroxypropyl cellulose, methyl cellulose, hydroxyethyl methyl cellulose, hydroxyethyl cellulose acetate, and hydroxyethyl ethyl cellulose; and at least partially ionizable cellulosic polymers at physiologically relevant pH, such as hydroxypropyl methyl cellulose acetate succinate (HPMCAS), hydroxypropyl methyl cellulose succinate, hydroxypropyl cellulose acetate succinate, hydroxyethyl methyl cellulose succinate, hydroxyethyl cellulose acetate succinate, hydroxypropyl methyl cellulose phthalate (HPMCP), hydroxyethyl methyl cellulose acetate succinate, hydroxyethyl methyl cellulose acetate phthalate, carboxyethyl cellulose, carboxymethyl cellulose, carboxymethyl ethyl cellulose, cellulose acetate phthalate (CAP), methyl cellulose acetate phthalate, ethyl cellulose acetate phthalate, hydroxypropyl cellulose acetate phthalate, hydroxypropyl methyl cellulose acetate phthalate, hydroxypropyl cellulose acetate phthalate succinate, hydroxypropyl methyl cellulose acetate succinate phthalate, hydroxypropyl methyl cellulose succinate phthalate, cellulose propionate phthalate, hydroxypropyl cellulose butyrate phthalate, cellulose acetate trimellitate, methyl cellulose acetate trimellitate, ethyl cellulose acetate trimellitate, hydroxypropyl cellulose acetate trimellitate, hydroxypropyl methyl cellulose acetate trimellitate, hydroxypropyl cellulose acetate trimellitate succinate, cellulose propionate trimellitate, cellulose butyrate trimellitate, cellulose acetate terephthalate, cellulose acetate isophthalate, cellulose acetate pyridinedicarboxylate, salicylic acid cellulose acetate, hydroxypropyl salicylic acid cellulose acetate, ethylbenzoic acid cellulose acetate, hydroxypropyl ethylbenzoic acid cellulose acetate, ethyl phthalic acid cellulose acetate, ethyl nicotinic acid cellulose acetate, and ethyl picolinic acid cellulose acetate.

According to an embodiment, "non-ionizable (neutral) non-cellulosic polymers" do not include ionizable non-cellulosic polymers such as carboxylic acid-functionalized vinyl polymers, such as the carboxylic acid functionalized polymethacrylates and carboxylic acid functionalized polyacrylates such as the Eudragit® manufactured by Evonik; amine-functionalized polyacrylates and polymethacrylates; proteins such as gelatin and albumin; and carboxylic acid functionalized starches such as starch glycolate.

In a preferred embodiment, the non-ionizable (neutral) non-cellulosic polymer is a vinyl polymer or copolymer substituted with at least one cyclic amido (lactam) group as substituent, also referred as a "polyvinyl lactam polymer".

1. According to an embodiment, the present invention concerns an amorphous solid dispersion of belinostat comprising:

a) Belinostat or a pharmaceutically acceptable salt, solvate or ester thereof;

b) At least one polyvinyl lactam polymer; and c) Optionally, at least one additive.

The preferred "polyvinyl lactam polymers" refers to polymers and copolymers comprising the following sub-unit:

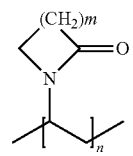

Where m is an integer chosen from 1, 2, 3 or 4 (β-, γ-, δ- or ε-lactam) and n represents the number of lactam repeating units in said sub-unit, which may be comprised between n=20 and n=30 000.

According to an embodiment, said polymer is water soluble. According to an embodiment, said polymer is a linear chain polymer.

"Linear chain polymer" as used herein refers to a straight-chain polymer which consists of a long string of repeating units which are joined end-to-end like links along said chain.

Where in formula (I), m is 2 and the polymer consists of sub-units (I), said polyvinyl lactam polymer is povidone. Povidone may also be named polyvidone, povidonum, PVP or poly(l-vinyl-2-pyrrolidone). Commercially available povidones are generally pharmaceutical grade products with different nominal K-values characterizing their molecular weight, including:

Povidone K12 (Kollidon® 12PF manufactured by BASF), Povidone K17 (Kollidon® 17PF manufactured by BASF; Plasdone® C-15 manufactured by ISP), Povidone K25 (Kollidon® 25 manufactured by BASF; Plasdone® K-25 marketed by ISP), Povidone K30 (Kollidon® 30 manufactured by BASF, Plasdone® K-29/32 manufactured by ISP), Povidone K30 with low peroxide grade (Kollidon® 30 LP), Povidone K90 (Kollidon® 90F manufactured by BASF; Plasdone® K-90, K-90 D and K-90M marketed by ISP).

Polyvinyl lactam polymers according to the invention also include copolymers which comprise the sub-unit (I) above. In particular, they include copolymers comprising the sub-unit (I) where m=2, and polyethenyl acetate sub-units, of formula:

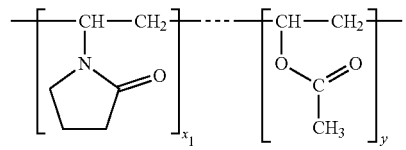

Such copolymers are named copovidone. Copovidone is a water soluble copolymer with a chain structure, made of 6 parts of vinyl pyrrolidone and 4 parts of vinyl acetate. Commercially available copovidone include Kollidon® VA64 (manufactured by BASF), Plasdone® S-630 (manufactured by ISP). Copovidone is also named copovidonum, copolyvidone, copovidon or PCV-VAc-copolymer (Polyvinylpyrrolidone excipients for pharmaceuticals Buhler et al 2005, Springer Verlag).

The polyvinyl lactam polymers of the invention also include the polymers and copolymers comprising the sub-unit (I), where m=4, (i.e.) including caprolactam rings.

In particular, they include Soluplus® copolymers as polyvinyl caprolactam polyvinyl acetate-polyethylene glycol graft copolymer, also named PCL-PVAc-PEG (manufactured by BASF) of formula:

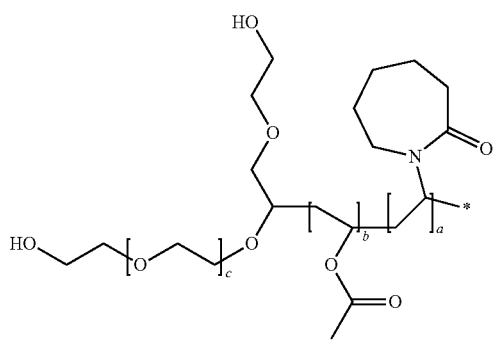

It should be further noted that the cross-linked polymers of formula (I) where m=2 are named crospovidone or insoluble polyvinylpyrrolidone (Bühler et al., above) and that they are therefore not encompassed by the linear and/or water soluble polyvinyl lactam polymers of the invention.

According to a particular embodiment, said polyvinyl lactam polymer is chosen from chain polymers and copolymers comprising the following sub-unit:

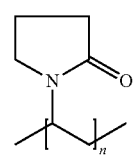

(II)

Where n is defined as in formula (I).

Exemplary polymers of formula (I) are detailed below:

| Status | Name | Synonym | Functional structure | Glass transition Temperature Tg |
|---|---|---|---|---|
| Excipients exemplified | PVP K30 | Polyvinylpyrrolidone, Povidone (K-value 30), PVP 29-32 MW~50 000 g/mol <br> PVP | Water-soluble Neutral (non cellulosic) | Tg 156° C.-163° C. |
|  | PVP VA64 | Copovidone, Vinylpyrrolidone-vinyl acetate copolymer MW~45 000 g/mol <br> PVP/VA | Water-soluble Neutral (non cellulosic) | Tg 101° C. |
|  | PVP K12 | Polyvinylpyrrolidone, Povidone (K-value 12), MW 2000-2500 g/mol | Water-soluble Neutral (non cellulosic) | Tg 101° C. |
|  | PVP K90 | Polyvinylpyrrolidone, Povidone (K-value 90), MW~1 250 000 K g/mol | Water-soluble Neutral (non cellulosic) | Tg 177° C. |
| Potential excipients suitable to improve amorphous spray dried dispersion | PVP K17 | Polyvinylpyrrolidone, Povidone (K-value 17), MW 9000-10 000 g/mol | Water-soluble Neutral (non cellulosic) | Tg 136° C. |
|  | PVP K25 | Polyvinylpyrrolidone, Povidone (K-value 25), MW 25 000-30 000 g/mol | Water-soluble Neutral (non cellulosic) | Tg 152° C. |

-continued

| Status | Name | Synonym | Functional structure | Glass transition Temperature Tg |
|---|---|---|---|---|
| | Soluplus® | 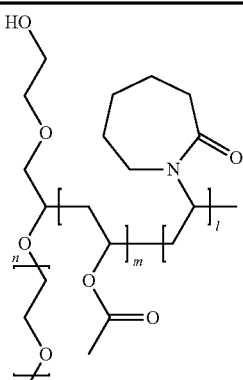

Polyvinyl caprolactam-polyvinyl acetate-polyethylene glycol graft co-polymer, PEG 6000/vinylcaprolactam/vinyl acetate 13/57/30 MW~188 000 g/mol | Water-soluble Neutral (non cellulosic) | Tg 70° C. |

In particular, polyvinyl lactam polymers are chosen from povidone polymers and copovidone copolymers; in particular: Soluplus®, PVP such as PVP K30, PVP K12, PVP K17, PVP K25, PVP K90, and PVP VA64; and anyone of their mixtures, such as 20/80, 30/70, 40/60, 50/50, 60/40, 70/30, or 80/20 mixture of PVP K30/PVP VA64, PVP K30/Soluplus, PVP K30/PVP K90.

More particularly, the polyvinyl lactam polymers are chosen from PVP K30, PVP K12 and PVP VA64, and the mixtures thereof; particularly PVP K30 and PVP VA64, and the mixtures thereof.

In one embodiment, the non-ionizable (neutral) non-cellulosic polymer is a polyvinyl alcohol (PVA) polymer.

In a particular embodiment, the PVA polymer is polyvinyl alcohol. In another embodiment, the PVA polymer is the polyvinyl alcohol-polyethylene glycol graft copolymer named Kollicoat® IR. The polymer of Kollicoat® IR consists of approximately 75% polyvinyl alcohol units and approximately 25% polyethylene glycol units.

According to an embodiment, the amorphous solid dispersion of belinostat may also comprise at least one additive.

According to an embodiment, said additive may be chosen from usual excipients that are commonly used in oral formulations and/or in solid dispersions. Suitable additives include in particular antioxidants, dispersing agents, pH modifiers, solubilizers, stabilizers, disintegrants or any mixture thereof.

pH modifiers such as acids, bases or buffers may be useful to reduce hydrolysis and/or chemical degradation but may also modify the dissolution rate; they include in particular KOH, NaOH, CaCO3, L-arginine, meglumine, Na carbonate, Na bicarbonate, citric acid or succinic acid, etc.

Anti-oxidants include in particular butylated hydroxytoluene (BHT), butylated hydroxyanisole (BHA), sodium metabisulfite (SMB), propyl gallate (PG), ascorbyl palmitate, dihydroxybenzoic acid, cysteine, ascorbic acid, alphatocopherol (Vit-E), etc. Suitable solubilizers are those additives that may improve in vitro dissolution profile (higher degree of supersaturation) and wettability but also may inhibit crystallization. The solubilizers may be anionic, cationic, amphoteric or non-ionic surfactants. They include in particular polysorbate (eg. Tween 80), sodium lauryl sulfate (SLS), Lauroyl polyoxyl-32 glycerides (Gelucire 44/14), D-a-tocopheryl polyethylene glycol 1000 succinate (TPGS), poloxamers (eg. Pluronic F127). Solubilizers may also include cyclodextrins such as sulfobutyl ether beta cyclodextrin or hydroxyl propyl beta cyclodextrin.

Stabilizers are those additives that may improve chemical and/or physical stability. Stabilizers include in particular amino-acids (eg. L-histidine, L-lysine, L-leucine, L-arginine, glycine, phenylalanine, tryptophan and tyrosine) or sugars (eg. sorbitol, glycerol, mannitol, xylitol, sucrose, trehalose).

When such additives are included as part of the dispersion itself, they may be comprised up to 25% of the dispersion.

According to an embodiment, the amorphous solid dispersion may comprise:
about 5 to 80% (weight) of belinostat; and
about 20 to 95% (weight) of said non-ionizable non-cellulosic polymer such as a polyvinyl lactam polymer;
particularly about 15 to 50% of belinostat (weight) and about 50 to 85% (weight) of said non-ionizable non-cellulosic polymer such as a polyvinyl lactam polymer.

The amorphous solid dispersion is physically stable in that belinostat may maintain its substantially amorphous form in the formulation upon storage for at least 2 years. To reduce the risk for recrystallization and ensure long term stability, belinostat ASDs of the inventions may also be stored in water vapor protective packaging to prevent water absorption into the dispersion.

The amorphous solid dispersions of the invention were also found chemically stable. Due to its hydroxamide group, belinostat in solution, as well as belinostat in amorphous state, is found to be very sensitive to hydrolysis and chemical degradation as other hydroxamic acid based HDAC inhibitors. Under amorphous state, belinostat main impurities are belinostat acid and belinostat dimer.

Belinostat acid ((E)-3-[3-(phenylsulfamoyl)phenyl]prop-2-enoic acid) is of formula:

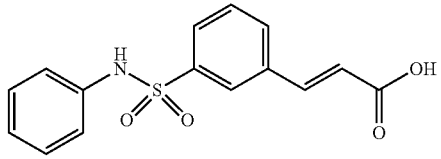 [SMILES: O=C(O)/C=C/c1cccc(S(=O)(=O)Nc2ccccc2)c1]

It is an intermediate in the synthesis of belinostat drug substance, a degradation product of belinostat upon hydrolysis of the hydroxamic acid function, and a metabolite (Finn et al. 2016).

Belinostat dimer ((E)-3-(3-(N-Phenylsulfamoyl)phenyl)-N-ME)-3-(3-(N-phenylsulfamoyl)-phenyl)acryloyl)oxy) acrylamide) is of formula:

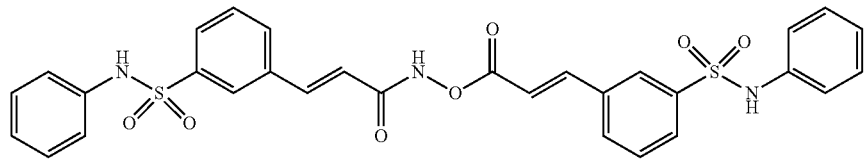 [SMILES: O=C(/C=C/c1cccc(S(=O)(=O)Nc2ccccc2)c1)NOC(=O)/C=C/c1cccc(S(=O)(=O)Nc2ccccc2)c1]

It is formed by degradation of belinostat by loss of hydroxamine. It is also a synthetic impurity during belinostat drug substance synthesis that is removed during process manufacture by a recrystallization step.

When solid dispersions are prepared using ionizable or neutral cellulosic polymers or ionizable non-cellulosic polymers, significant chemical degradation in belinostat acid or belinostat dimer may be observed upon storage.

Surprisingly, when non-cellulosic neutral polymers such as polyvinylactam polymers are used, the resulting amorphous solid dispersion of the invention is chemically stable in that the degradation of belinostat into its two main impurities in the amorphous solid dispersion formulation is maintained within the following upper limits:

Less than 0.2% of belinostat acid and/or belinostat dimer, upon release testing; and/or Less than 2% of belinostat acid and/or belinostat dimer upon storage for at least 18 months, preferably at least 24 months, most preferably at least 36 months during storage in ICH (International Council for Harmonization of Technical Requirements for Pharmaceutical for Human Use) conditions.

The amorphous solid dispersions of the invention provide enhanced solubility and dissolution characteristics, compared to crystalline drug when tested in in vitro dissolution tests.

In some embodiments, compositions, when tested in in vitro test, at a supersaturation level of 5 fold, exhibit an increase in belinostat solubility at 90 min at least 1.5 times higher compared to non-dispersed crystalline drug tested in the same conditions, typically at least 2 times, or even at least 2.5 times higher. Given the extremely low aqueous solubility of belinostat, such large enhancement of solubility using dispersions of the invention are rather surprising.

Within the scope of the invention, the amorphous solid dispersions, presenting improved in vitro dissolution properties, also significantly improve plasma exposure and bioavailability in vivo.

When tested in vivo, a composition within the scope of the invention exhibits either a $C_{max}$ or an AUC that is at least 1.25 times higher than the corresponding $C_{max}$ or AUC exhibited by a composition comprising an equivalent quantity of undispersed crystalline drug. Preferably the $C_{max}$ or AUC at least 1.5 higher, more preferably 2 times higher.

Such compositions can also be said to have a relative bioavailability of at least about 1.25 compared to undispersed crystalline drug, typically up to at least 2 times.

According to a second object, the present invention also concerns the process of preparation of the amorphous solid dispersion of the invention.

The amorphous solid dispersion may be prepared by any known methods in the art, including spray-drying, hot-melt extrusion (HME), and precipitation from solution on addition of a non-solvent. Preferably the method is the spray-drying method.

According to an embodiment, said process comprises the steps of:

Preparing a solution of belinostat and said non-ionizable non-cellulosic polymer such as polyvinyl lactam polymer in a solvent, optionally with said optional additives; and Spray-drying said solution.

Spray-drying is a method generally well known in the art and typically involves transformation of a solution into a dried form by spraying the solution into a hot drying medium. The spray dried product is typically in the form of a powder consisting of single particles or agglomerates, depending upon the physical and chemical properties of the formulation and the dryer design and operation. The basic technique generally includes the following four steps: a) atomization of the solution into a spray; b) spray-gas contact; c) drying of the spray, and d) separation of the dried product from the drying gas.

The actual spray drying generally involves the atomization of a solution (feedstock) into a spray of droplets, and contacting the droplets with hot gas in a drying chamber. The droplets can be produced by, for example, nozzle atomizers. Evaporation of moisture from the produced droplets and formation of dry particles may proceed under controlled temperature and gas flow conditions. When the droplets are small enough and the chamber is large enough, the droplets generally dry before they reach the wall of the chamber. The resulting product is collected as a free-flowing material. Powder may be discharged continuously from the drying chamber. Operating conditions and spray dryer design are generally selected according to the drying characteristics of the product and powder specification.

Spray dryers generally include a feedstock pump, an atomizer, a gas heater, a gas disperser, a drying chamber, and systems for exhaust gas cleaning and powder recovery. An example spray drying system includes drying gas introduced into a pre-filter. In one aspect, the drying gas is nitrogen, and avoids the presence of oxygen. The drying gas then passes through a fan and a heater, which may be an electric heater. The drying gas then passes through an inlet gas temperature gauge monitors the inlet gas temperature before it is introduced into a drying chamber via a ceiling gas dispenser. Redundant filtration may be employed to ensure product quality.

The solvent is generally chosen among organic solvents that may solubilize both belinostat and the non-ionizable non-cellulosic polymer such as polyvinyl lactam polymer. Suitable solvents include methanol, acetone, chloroform, ethanol, dichloromethane, water.

Generally, solutions at 5-50% of solid weight are prepared.

According to an alternative embodiment, said process comprises the steps of:
  Mixing belinostat and said non-ionizable non-cellulosic polymer such as polyvinyl lactam polymer eventually with optional additives; and
  Extruding the mixture by using a temperature-controlled extruder.

According to either embodiments of the process, the amounts of belinostat and the polymer are generally used in their respective ratio, as desired in the amorphous solid dispersion discussed above.

The amorphous solid dispersion of the invention is suitable for oral administration of belinostat.

According to a third object, the present invention thus concerns a pharmaceutical composition comprising the amorphous solid dispersion of belinostat of the invention, optionally with one or more pharmaceutically acceptable excipients.

The compositions may conveniently be prepared by any of the methods well known in the pharmaceutical art, for example, as described in *Remington: The Science and Practice of Pharmacy*, 20$^{th}$ ed.; Gennaro, A. R., Ed.; Lippincott Williams & Wilkins: Philadelphia, Pa., 2000.

Formulations which are suitable to be administered orally to a patient include discrete units such as capsules, soft or hard gelatine capsules, tablets, each containing a predetermined amount of belinostat and/or of the amorphous solid dispersion of belinostat. They also include powders or granules; multiparticulates, suspensions in an aqueous liquid or a non-aqueous liquid. Pharmaceutical compositions can be optionally coated.

"Pharmaceutically" or "pharmaceutically acceptable" refer to molecular entities and compositions that do not produce an adverse, allergic or other undesired reaction when administered to an animal, or a human, as appropriate.

As used herein, "pharmaceutically acceptable excipient" includes in particular diluents, adjuvants, carriers, or vehicles. The use of such ingredients for pharmaceutical active substances is well known in the art.

The amorphous solid dispersion of belinostat may be administered in unit dosage forms, wherein the term "unit dosage" means a single dosage which is capable of being administered to a patient, and which can be readily handled and packaged.

The daily dose according to the invention may be achieved by administering half a unit dosage form, a single unit dosage form or two or more unit dosage forms, according to the marketed unit dosage form, the daily dose to be administered and the frequency of administration that is prescribed by the practitioner.

According to another object, the present invention also concerns the amorphous solid dispersion of belinostat of the invention for use in treating and/or preventing cancer.

As used herein, "cancer" refers to various forms of cancers, including tumors or leukemia. Cancers of breast, prostate, lung, colon, bladder, brain, stomach, kidney, liver, ovary, mouth, skin, intestine, uterine, head and neck, throat, hematopoietic and lymphoid tissues, and blood are encompassed herein. Lymphoma (ie) cancer of blood cells, including Hodgkin's lymphomas, non-Hodgkin lymphomas and multiple myeloma is particularly intended, and more particularly relapsed or refractory peripheral T-cell lymphoma (PTCL).

The identification of those subjects who are in need of treatment of herein-described diseases and conditions is well within the ability and knowledge of one skilled in the art. A clinician skilled in the art can readily identify, by the use of clinical tests, physical examination, genetic tests and medical/family history, those subjects who are in need of such treatment.

Actual dosage levels of the solid dispersion of belinostat of the invention may be varied so as to obtain an amount of active ingredient that is effective to obtain a desired therapeutic response for a particular composition and method of administration. The selected dosage level therefore depends on the desired therapeutic effect, on the route of administration, on the desired duration of treatment and other factors, e.g. the condition of the patient.

A therapeutically effective amount can be readily determined by the attending physician, as one skilled in the art, by the use of conventional techniques and by observing results obtained under analogous circumstances. In determining the therapeutically effective amount, a number of factors are considered by the attending physician, including, but not limited to: the species of subject; its size, age, and general health; the specific disease involved; the degree of involvement or the severity of the disease; the response of the individual subject; the particular compound administered; the mode of administration; the bioavailability characteristic of the preparation administered; the dose regimen selected; the use of concomitant medication; and other relevant circumstances.

The amount of the amorphous solid dispersion which is required to achieve the desired biological effect will vary depending upon a number of factors, including the dose of the drug to be administered, the type and progression of disease, the disease state of the patient and the route of administration.

In the context of the invention, the term "treating" or "treatment", as used herein, means reversing, alleviating, inhibiting the progress of, or preventing the disorder or condition to which such term applies, or one or more symptoms of such disorder or condition.

"Therapeutically effective amount" means an amount of a compound/pharmaceutical composition according to the present invention effective in producing the desired therapeutic effect.

According to the invention, the term "patient", or "patient in need thereof", is intended for a human or non-human mammal affected or likely to be affected with the above disorders. Preferably, the patient is a human.

FIGURES

FIG. 1 illustrates the comparative pharmacokinetics results in dog, of example 5.

The following examples are given as an illustration of the present invention.

EXAMPLES

Example 1: Bioavailability of Oral Solid Dosage Form of Belinostat

A dog PK study was performed to compare plasma exposure and bioavailability of 5 different oral solid dosage forms of belinostat. Formulations A, B, C, D and E (composition detailed in the Table 1) were administered by oral gavage on 5 female Beagle dogs (7.0-9.0 Kg) in fasted state at a fixed dose of 50 mg per dog (equivalent to 6.5 to 10.2 mg/kg). Animals were dosed once with each formulation with one week washout period between each dosing. Intravenous dosing was performed for absolute bioavailability calculation by a slow bolus injection into the cephalic vein.

Blood samples were taken into heparinized tubes after each dose at the following timepoints: 5, 15 and 30 min, 1, 3, 6, 12, 24 and 36 hours from the saphenous or cephalic veins. Belinostat plasma concentrations were measured using a validated bioanalytical method (solid phase extraction, UHPLC-MS/MS, concentration range: 2-2000 ng/mL). Pharmacokinetic parameters were derived from the individual plasma concentration profiles by non-compartmental analysis using WinNonlin Professional (version 4.1.).

$C_{max}$, $AUC_{0-24}$ and bioavailability (F %), calculated for each dog and then averaged for the test population, are reported in Table 1.

The results show that neither conventional capsule (Formulation A) nor micronized belinostat in tablet/capsules (Formulations B, D and E) or in liquid lipidic suspension (Formulation C) formulations are suitable in terms of improvement of bioavailability of belinostat compared to crystalline form and justify the need for a specific enabling technology to increase solubility and thus bioavailability.

Example 2: Amorphous Solid Dispersion

Different ASDs of belinostat and polymer were prepared by spray drying, according to the following procedure:

Solvent solutions of belinostat with different polymers (selected from HPMCAS-L, HPMCAS-M, HPMCAS-H, HPMC E3, PVP K12, PVP K30, PVP VA 64, Eudragit L100, Eudragit E PO, Eudragit S100, HPMCP HP 55S, CAP and mixture of PVP K30/PVP K90) were prepared in methanol, methanol/water or acetone (3-10% solid weight in solvent) and spray dried using Bend Research Custom Built Lab Scale Spray Dryer [Bend Research, Bend Oreg., Equipment ID #BRI-EQ-0036] to obtain fine particle of spray dried solid dispersion on 7.5-10 g scale. Some ASDs with HPMCAS were tested with some additives: pH modifier [KOH, CaCO3 Na bicarbonate], and ASDs with PVP K30 were tested with anti-oxidant [BHT], or stabilizers [L-histidine]. A mixture of PVP K30 and PVP K90 at a ratio of 75/25 was also tested. When an additive was used, it was dissolved and mixed with belinostat and polymer in the

TABLE 1

Pharmacokinetic parameters of different oral solid dosage form of belinostat in dog

| Dose | IV Arginine formulation | Formulation A Neat belinostat in capsule | Formulation B Tablet prototype | Formulation C Suspension in capsule | Formulation D Granulate in capsule I | Formulation E Granulate in capsule II |
|---|---|---|---|---|---|---|
| Dose route | IV | Oral | Oral | Oral | Oral | Oral |
| Composition | Solution of belinostat at 50 mg/mL containing 10% L-arginine in SWFI | 50 mg Unmicronized belinostat in capsule | 50 mg tablets (55.56% Micronized Belinostat, 16% Pregelatinized Starch, 16.24% Microcrystalline Cellulose, 2.2% povidone, 6% crospovidone, 3% SLS, 0.25% colloidal silicon dioxide, 0.75% magnesium stearate) | 50 mg capsules (10% micronized belinostat in suspension in liquid lipidic vehicle: 80% Miglyol 812N and 10% Lecithin) | 50 mg capsules (83% micronized belinostat, 4.5% povidone K12, 2.5% SLS, 10% poloxamer 188) | 50 mg capsules (60% micronized belinostat, 37% maltodextrin, 3% SLS) |
| Cmax (ng/mL) | 5830 | 183 | 309 | 154 | 176 | 218 |
| AUC $_{0-24}$ (ng*hr/ml) | 2700 | 428 | 429 | 396 | 345 | 323 |
| Bioavailability | 100% | 15.9% | 15.9% | 14.7% | 12.8% | 12.0% |

All the oral forms of administration resulted in similar exposure levels with $AUC_{0-24h}$ being from 12% to 16% of the intravenous dosage. The different types of oral administration did not change the exposure profiles and none enhanced bioavailability compared to neat belinostat in capsules.

solvent solution before spray drying. The following conditions were used for all experiments; atomizing pressure 100-140 psi, gas flow rate: 450-475 g/min, solution flowrate: 10-30 g/min, inlet temperature: 81-166° C.

After a secondary drying overnight at 40° C. 15% RH in a convection tray dryer, the different ASD were characterized for physical stability (XRPD, Tg versus Relative humidity), chemical stability (impurity by HPLC after 1 week 40° C./75% RH) and in vitro dissolution.

The different formulations were prepared and tested as summarized in Table 2 below. Unless mentioned otherwise in Table 2, the ASDs contained 25% belinostat. Some formulations were tested at 15% to 50% drug loading. Theoretically lower or higher drug loading could be envisaged.

Example 3: Physical Stability

Amorphous or crystalline state of freshly prepared spray dried dispersions described in Example 2 was assessed by Powder X-ray diffraction (XRPD). The same analysis was repeated after 1 week storage at 40° C. and 75% relative humidity in open conditions. XRPD patterns were obtained with Rigaku MiniFlex 600 X-Ray diffractometer operating with a copper anode ($K_{\alpha 1}$=1.5060 Å; $K_{\alpha 2}$=1.54439 Å), generator set at 45 kV and 15 mA, in 2-theta range 3-40° 2θ, scanned at a rate of 2.5° 2θ per minute in continuous scanning mode, and using a D/teX Ultra high speed detector.

Table 2 describes Crystalline/Amorphous state of the different ASD prepared with belinostat. All ASD diffractograms displayed a broad amorphous halo with the absence of sharp signals as a representative example. The disappearance of peaks of belinostat crystals in spray dried samples demonstrates that the different spray dried dispersions are substantially amorphous. In contrast, amorphous belinostat, not stabilized with a polymer, undergoes recrystallization upon storage.

After 1 week storage at 40° C. and 75% relative humidity (open), except for spray dried belinostat (without polymer), all spray dried dispersions were substantially amorphous. They showed a general good physical stability of belinostat in amorphous form when dispersed in various polymers.

To also evaluate the physical stability of prepared ASDs, glass transition temperature (Tg) was determined at two relative humidity (RH) conditions (<5% and 75% RH) by modulated differential scanning calorimetry (m-DSC).

DSC curves were recorded using a TA Instruments Q2000 differential scanning calorimeter. Samples were heated under nitrogen flow from 0 to 200° C. at 2.5° C.±1.5° C./min in non-hermetically sealed pan for <5% RH analysis or from 0 to 130° C. at 2.5° C.±1.5° C./80 sec in hermetically sealed pan for 75% RH analysis.

Table 2 describes Tg of the different ASD prepared with belinostat.

Amorphous belinostat has relatively low glass transition temperature (Tg), which is about 53° C. Since the molecules even in a glassy amorphous state have some mobility, it is known in the art that it is beneficial that the glass transition temperature of the ASD is higher than the actual storage conditions (at least 20° C. higher and more preferably at least 40° C. higher).

Comparing all recorded Tg values of amorphous spray dried dispersions, PVP K12, PVP K30, PVP VA 64 were found to have satisfactory glass transition temperatures (≤100° C. at <5% RH %).

Thus, ASDs of belinostat with polyvinyl lactam polymers exhibit good physical stability in amorphous state.

Example 4: Chemical Stability

Due to hydroxamide function, belinostat is easily hydrolyzed, so it is challenging to develop a chemically stable ASD.

Purity of each batch of ASD was tested by HPLC analysis on sample just after preparation and after one week storage in accelerated stability conditions: 40° C./75% RH open or closed. In closed conditions, ASDs were placed in closed bottles (heat induction seal) containing 1 g SORB-IT desiccant canister.

HPLC-analysis was performed using an Agilent 1100 or 1200 system with binary or quaternary pump, a diode array detector, a refrigerated autosampler, and column oven. Data analysis was performed using Empower 3 software. The column used was Zorbax Bonus RP 4.6×150 mm (3.5 µm). Acetonitrile/20 mM Potassium phosphate buffer pH 3.0 was used as mobile phase with a gradient concentration at a flow rate of 1.0 mL/min; UV detection was used at a wavelength of 220 nm.

Belinostat leads to two main impurities: belinostat acid (Bel-Acid) and belinostat dimer (Bel-dimer).

Table 2 summarizes the purity profile of each spray dried dispersion indicating area % of total impurity and area % of belinostat acid (Bel-Acid) and belinostat dimer (Bel-dimer) impurities.

For most ASDs prepared, dimer impurity content and total impurity values are initially low but impurity level significantly increases with time upon storage in accelerated stability conditions. Variability in impurity formation, particularly dimer impurity is observed depending on the associated polymer.

Cellulosic (HPMCAS, HPMC, HPMCP, CAP) based ASDs (formulations 3-12) provided rapid chemical degradation. To overcome a possible acid catalyzed hydrolysis of the hydroxamide by the acid function of the HPMCAS-M polymer, pH modifiers additive were tested (formulations 5 & 6). It resulted in higher chemical degradation so this approach was not satisfactory either. Other polymers (non-cellulosic ionizable), such as Eudragit® (formulations 23-25), were not satisfactory either since they lead to increased chemical degradation.

However, the results show that only non-ionizable (neutral) non-cellulosic polymers such as polyvinyl lactam polymers (such as PVP VA64, PVP K12 and PVP K30 alone, mixed with PVP K90 or with an additive, such as a stabilizer) can significantly prevent/reduce dimer formation contrary to other polymers (formulations 13-22).

Example 5: Non-Sink In Vitro Dissolution

Dissolution of spray dried materials of belinostat has been tested in vitro, in non-sink conditions, in order to evaluate the ability of formulations to achieve supersaturation and sustainability of supersaturation relative to crystalline drug.

Dissolution was assessed using micro-centrifuge method (Curatolo et al. Pharm Res 2009:26(6):1419-1431). Micro-centrifuge dissolution method consisted of introducing a 1.8 mg equivalent belinostat as ASD into an empty micro-centrifuge tube and add 1.8 mL total volume dissolution media (PBS pH 6.5 with 0.5 wt % Simulated Intestinal Fluid) to achieve a theoretical maximum belinostat concentration in solution of 1000 µg/mL. For some formulations (marked with* in Table 2), ASDs were first exposed in pH 2.0 gastric media at 2000 µg/mL for 30 min before to be transferred to the PBS pH 6.5 with 0.5 wt % Simulated Intestinal Fluid at a final theoretical maximum belinostat concentration in solution of 1000 µg/mL. Tubes were placed at 37° C. Aliquot (50 µL) were taken from supernatant after centrifugation 15 800 g for 1 min at each time point (5, 10, 20, 45, 90 and 1200 minutes). Between each time point, solids in the centrifuge tube were resuspended by mixing the sample continuously on the vortex mixer for 30 s and the tube was placed back at 37° C. Aliquot samples were diluted using acetonitrile and drug concentration was determined by HPLC.

Table 2 summarizes the $C_{90min}$ and $C_{1200min}$ which represents the concentrations in dissolution media obtained after 90 min and 1200 minutes.

Using the ASDs of the invention, concentration of belinostat in solution after 90 minutes is 2 to 3.5 fold higher compared to non-dispersed crystalline drug. Similar solubility values are obtained after 1200 min and show the ability of the selected polymers to maintain good supersaturated level with time.

TABLE 2

Summary of physical stability, chemical stability and dissolution results of different belinostat amorphous solid dispersions (ASD)

| | | Physical Stability | | | Chemical stability (impurity area %) | | | Dissolution | |
|---|---|---|---|---|---|---|---|---|---|
| Formulations | Tg (°C.) <5% RH[a] Tg (°C.) 75% RH[b] | | XRPD initial | XRPD 1 week 40/75 open | Initial | 1 week 40/75 open | 1 week 40/75 closed | Dissolution $C_{90\,min}$ µg/mL | Dissolution $C_{20\,h}$ µg/mL |

Controls

| 1 | Crystalline | NA | NA | Crystalline | Crystalline | Bel Acid <0.05 Bel Dimer NA Total imp <0.05 | — | — | 270 | 310 |
| 2 | Spray dried belinostat | 53 | Not found | Partially crystalline | Crystalline | Bel Acid 0.05 Bel Dimer 0.48 Total imp 0.59 | Bel Acid 0.10 Bel Dimer 0.25 Total imp 0.42 Recrystallization observed | Bel Acid 0.10 Bel Dimer 1.34 Total imp 1.49 | 363 Recrystallization observed | 387 |

Cellulosic polymers (Non-ionizable & ionizable) based ASD

| 3 | HPMCAS-L | 81 | 37 | Amorphous | Amorphous | Bel Acid ND Bel Dimer 0.19 Total imp 0.45 | Bel Acid 0.14 Bel Dimer 2.07 Total imp 2.44 | Not performed | 980 | 920 |
| 4 | HPMCAS-M | 83 | 38 | Amorphous | Amorphous | Bel Acid ND Bel Dimer 0.20 Total imp 0.39 | Bel Acid 0.10 Bel Dimer 1.77 Total imp 2.11 | Not performed | 950 | 920 |
| 5 | HPMCAS-M + 1Meq.KOH | 87 | 37 | Amorphous | Amorphous | Bel Acid ND Bel Dimer 0.09 Total imp 1.95 | Bel Acid 2.86 Bel Dimer 2.21 Total imp 8.80 | Bel Acid 0.19 Bel Dimer 0.32 Total imp 2.12 | 785 | 770 |
| 6 | HPMCAS-M + 2% CaCO3 | 80 | 33 | Amorphous | Amorphous | Bel Acid 0.09 Bel Dimer 0.99 Total imp 1.72 | Bel Acid 0.17 Bel Dimer 1.85 Total imp 2.81 | Bel Acid 0.09 Bel Dimer 1.23 Total imp 2.12 | 896 | 883 |
| 7 | HPMCAS-M (50% API) | 71 | 42 | Amorphous | Amorphous | Bel Acid ND Bel Dimer 0.17 Total imp 0.45 | Bel Acid 0.13 Bel Dimer 1.76 Total imp 1.98 | Bel Acid ND Bel Dimer 0.71 Total imp 0.81 | 922 | 909 |
| 8 | HPMCAS-M (75% API) | 60 | 27 | Amorphous | Amorphous | Bel Acid ND Bel Dimer 0.21 Total imp 0.59 | Bel Acid 0.22 Bel Dimer 1.88 Total imp 2.40 | Bel Acid 0.08 Bel Dimer 0.87 Total imp 1.14 | 774 | 789 |
| 9 | HPMCAS-H | 80 | 42 | Amorphous | Amorphous | Bel Acid 0.04 Bel Dimer 0.18 Total imp 0.28 | Bel Acid 0.16 Bel Dimer 1.37 Total imp 1.69 | Bel Acid 0.07 Bel Dimer 0.83 Total imp 0.95 | 602 | 596 |
| 10 | HPMC E3 | 93 | 30 | Amorphous | Amorphous | Bel Acid ND Bel Dimer 0.10 Total imp 0.30 | Bel Acid 0.19 Bel Dimer 0.62 Total imp 1.18 | Not performed | 700 | 780 |
| 11 | HPMCP HP55S | 100 | 46 | Amorphous | Amorphous | Bel Acid 0.04 Bel Dimer 0.17 Total imp 0.27 | Bel Acid 0.38 Bel Dimer 1.53 Total imp 1.96 | Bel Acid 0.06 Bel Dimer 0.84 Total imp 0.94 | 751 | 759 |

TABLE 2-continued

Summary of physical stability, chemical stability and dissolution results of different belinostat amorphous solid dispersions (ASD)

| | | Physical Stability | | | | Chemical stability (impurity area %) | | | Dissolution | |
|---|---|---|---|---|---|---|---|---|---|---|
| | Formulations | Tg (°C.) <5% RH[a] | Tg (°C.) 75% RH[b] | XRPD initial | XRPD 1 week 40/75 open | Initial | 1 week 40/75 open | 1 week 40/75 closed | Dissolution C$_{90\ min}$ µg/mL | Dissolution C$_{20\ h}$ µg/mL |
| 12 | CAP | 110 | 46 | Amorphous | Amorphous | Bel Acid 0.03<br>Bel Dimer 0.22<br>Total imp 0.31 | Bel Acid 0.27<br>Bel Dimer 2.14<br>Total imp 2.46 | Bel Acid 0.06<br>Bel Dimer 0.68<br>Total imp 0.78 | 723 | 715 |
| | | | | | Non-ionizable (neutral) non-cellulosic polymers based ASD | | | | | |
| 13 | PVP K30 (15% API) | 146 | 30 | Amorphous | Amorphous | Bel Acid 0.04<br>Bel Dimer 0.03<br>Total imp 0.24 | Bel Acid 0.14<br>Bel Dimer 0.18<br>Total imp 0.56 | Bel Acid 0.05<br>Bel Dimer 0.04<br>Total imp 0.31 | 965 | 1020 |
| 14 | PVP K30 (25% API) | 139 | 43 | Amorphous | Amorphous | Bel Acid 0.04<br>Bel Dimer 0.05<br>Total imp 0.15 | Bel Acid 0.14<br>Bel Dimer 0.30<br>Total imp 0.52 | Bel Acid 0.05<br>Bel Dimer 0.13<br>Total imp 0.24 | 806 | 837 |
| 15 | PVP K30 (50% API) | 107 | 49 | Amorphous | Amorphous | Bel Acid 0.04<br>Bel Dimer 0.04<br>Total imp 0.26 | Bel Acid 0.10<br>Bel Dimer 0.46<br>Total imp 0.83 | Bel Acid 0.05<br>Bel Dimer 0.18<br>Total imp 0.44 | 813 | 809 |
| 16 | PVP K30 low peroxide grade | 140 | 39 | Amorphous | Amorphous | Bel Acid 0.03<br>Bel Dimer 0.03<br>Total imp 0.27 | Bel Acid 0.09<br>Bel Dimer 0.20<br>Total imp 0.55 | Bel Acid 0.05<br>Bel Dimer 0.06<br>Total imp 0.33 | 933 | 975 |
| 17 | PVP K30 + 2% BHT | 135 | 41 | Amorphous | Amorphous | Bel Acid 0.03<br>Bel Dimer 0.03<br>Total imp 0.24 | Bel Acid 0.11<br>Bel Dimer 0.20<br>Total imp 0.56 | Bel Acid 0.05<br>Bel Dimer 0.05<br>Total imp 0.29 | 960 | 1006 |
| 18 | PVP K30 + 2% NaHCO$_3$ | 141 | 38 | Amorphous | Amorphous | Bel Acid 0.07<br>Bel Dimer 0.03<br>Total imp 0.32 | Bel Acid 0.26<br>Bel Dimer 0.15<br>Total imp 0.85 | Bel Acid 0.11<br>Bel Dimer 0.03<br>Total imp 0.47 | 1000 | 979 |

TABLE 2-continued

Summary of physical stability, chemical stability and dissolution results of different belinostat amorphous solid dispersions (ASD)

| | | Physical Stability | | | | Chemical stability (impurity area %) | | | Dissolution | |
|---|---|---|---|---|---|---|---|---|---|---|
| | Formulations | Tg (°C.) <5% RH[a] | Tg (°C.) 75% RH[b] | XRPD initial | XRPD 1 week 40/75 open | Initial | 1 week 40/75 open | 1 week 40/75 closed | Dissolution $C_{90\,min}$ μg/mL | Dissolution $C_{20\,h}$ μg/mL |
| 19 | PVP VA64 | 108 | 36 | Amorphous | Amorphous | Bel Acid ND Bel Dimer 0.04 Total imp 0.20 | Bel Acid 0.07 Bel Dimer 0.31 Total imp 0.58 | Not performed | 530 | 570 |
| 20 | PVP K12 | 100 | 0 | Amorphous | Amorphous | Bel Acid <0.05 Bel Dimer <0.05 Total imp 0.11 | Bel Acid 0.06 Bel Dimer 0.21 Total imp 0.33 | Bel Acid <0.05 Bel Dimer 0.10 Total imp 0.24 | 597* | 714* |
| 21 | PVP K30 + 5% L-histidine | 121 | 33 | Amorphous | Amorphous | Bel Acid <0.05 Bel Dimer <0.05 Total imp 0.06 | Bel Acid 0.07 Bel Dimer 0.17 Total imp 0.33 | Bel Acid 0.06 Bel Dimer 0.12 Total imp 0.25 | 788* | 815* |
| 22 | PVP K30/PVP K90 | 131 | 24 | Amorphous | Amorphous | Bel Acid <0.05 Bel Dimer 0.09 Total imp 0.15 | Bel Acid 0.06 Bel Dimer 0.31 Total imp 0.44 | Bel Acid 0.05 Bel Dimer 0.18 Total imp 0.31 | 577* | 727* |
| | | | | | Ionizable non-cellulosic polymers based ASD | | | | | |
| 23 | Eudragit L100 | 151 | Phase Separation | Amorphous | Amorphous | Bel Acid ND Bel Dimer 0.22 Total imp 0.86 | Bel Acid 0.44 Bel Dimer 1.33 Total imp 1.93 | Not performed | 960 | 940 |
| 24 | Eudragit E PO | 62 | 33 | Amorphous | Amorphous | Bel Acid ND Bel Dimer 0.06 Total imp 0.74 | Bel Acid 0.79 Bel Dimer 0.29 Total imp 1.84 | Bel Acid 0.13 Bel Dimer 0.23 Total imp 0.83 | 173 | 211 |
| 25 | Eudragit S100 | Not determinable | Not determinable | Amorphous | Amorphous | Bel Acid 0.05 Bel Dimer 0.26 Total imp 0.37 | Bel Acid 0.54 Bel Dimer 1.08 Total imp 1.67 | Bel Acid 0.10 Bel Dimer 0.75 Total imp 0.89 | 921 | 876 |

ND: non detected

*formulations for which in vitro dissolution was first in pH 2.0 gastric media for 30 min before to be diluted in PBS pH 6.5 media.

CONCLUSIONS

In terms of chemical stability, the formation of the dimer impurity was variable depending on the polymers used.

The in vitro dissolution data of the various belinostat amorphous spray-dried dispersions of the invention with a non-ionizable (neutral) non-cellulosic polymer such as a polyvinyl lactam polymer exhibit a large solubility enhancement compared with non-dispersed crystalline belinostat and show that the dispersions markedly improved the dissolution rate of the drug.

It appears that polymers belonging to polyvinyl lactam group provide good chemical stability of belinostat in amorphous state. Others polyvinyl lactams polymers such as Soluplus®, PVP others molecular weight (PVP K17, PVP K25) are expected to be also suitable polymers.

The above results show that only the polymers of the polyvinyl lactam class lead to outstanding chemical stability, together with a suitable Tg, good physical stability and satisfactory dissolution profile.

The polyvinyl lactam polymers were unexpectedly found to achieve a satisfactory dissolution, together with a lower rates of dimer formation.

Three ASDs were also tested for longer stability duration (1, 3 and 6 Months at 5° C. and real time (25/60 open & closed) and accelerated (30/65 closed) stability conditions (see Table 3 below).

TABLE 3

Supportive chemical stability 6 months PVP VA64, PVP K30 and HPMCAS-M ASD

| Weeks | 25° C. 60% RH closed (desiccant) | 25° C. 60% RH open | 30° C. 65% RH closed (desiccant) | Fridge 2-8° C. (open) |
|---|---|---|---|---|
| | \multicolumn{4}{c}{Chemical stability (impurity area %)} | | | |
| | \multicolumn{4}{c}{PVP VA 64} | | | |
| 0 | Bel Acid 0.05 | Bel Acid 0.05 | Bel Acid 0.05 | Bel Acid 0.05 |
| | Bel Dimer 0.06 | Bel Dimer 0.06 | Bel Dimer 0.06 | Bel Dimer 0.06 |
| | Total imp 0.16 | Total imp 0.16 | Total imp 0.16 | Total imp 0.16 |
| 4 | Bel Acid <0.05 | Bel Acid <0.05 | Bel Acid 0.04 | Bel Acid 0.03 |
| | Bel Dimer 0.10 | Bel Dimer 0.12 | Bel Dimer 0.11 | Bel Dimer 0.04 |
| | Total imp 0.20 | Total imp 0.22 | Total imp 0.21 | Total imp 0.12 |
| 12 | Bel Acid 0.06 | Bel Acid 0.07 | Bel Acid 0.07 | Bel Acid not tested |
| | Bel Dimer 0.16 | Bel Dimer 0.22 | Bel Dimer 0.21 | Bel Dimer not tested |
| | Total imp 0.26 | Total imp 0.33 | Total imp 0.33 | Total imp not tested |
| 24 | Bel Acid 0.05 | Bel Acid 0.12 | Bel Acid 0.07 | Bel Acid 0.04 |
| | Bel Dimer 0.23 | Bel Dimer 0.34 | Bel Dimer 0.37 | Bel Dimer 0.06 |
| | Total imp 0.44 | Total imp 0.63 | Total imp 0.62 | Total imp 0.35 |
| | \multicolumn{4}{c}{HPMCAS-M} | | | |
| 0 | Bel Acid 0.04 | Bel Acid 0.04 | Bel Acid 0.04 | Bel Acid 0.04 |
| | Bel Dimer 0.22 | Bel Dimer 0.22 | Bel Dimer 0.22 | Bel Dimer 0.22 |
| | Total imp 0.31 | Total imp 0.31 | Total imp 0.31 | Total imp 0.31 |
| 4 | Bel Acid 0.05 | Bel Acid 0.08 | Bel Acid 0.03 | Bel Acid 0.04 |
| | Bel Dimer 0.59 | Bel Dimer 0.84 | Bel Dimer 0.74 | Bel Dimer 0.27 |
| | Total imp 0.69 | Total imp 0.98 | Total imp 0.83 | Total imp 0.36 |
| 12 | Bel Acid 0.07 | Bel Acid 0.14 | Bel Acid 0.09 | Bel Acid not tested |
| | Bel Dimer 0.88 | Bel Dimer 1.48 | Bel Dimer 1.28 | Bel Dimer not tested |
| | Total imp 1.00 | Total imp 1.69 | Total imp 1.42 | Total imp not tested |
| 24 | Bel Acid 0.08 | Bel Acid 0.33 | Bel Acid 0.16 | Bel Acid 0.05 |
| | Bel Dimer 1.48 | Bel Dimer 2.69 | Bel Dimer 2.58 | Bel Dimer 0.36 |
| | Total imp 1.65 | Total imp 3.14 | Total imp 2.85 | Total imp 0.53 |
| | \multicolumn{4}{c}{PVPK30} | | | |
| 0 | Bel Acid 0.04 | Bel Acid 0.04 | Bel Acid 0.04 | Bel Acid 0.04 |
| | Bel Dimer 0.05 | Bel Dimer 0.05 | Bel Dimer 0.05 | Bel Dimer 0.05 |
| | Total imp 0.15 | Total imp 0.15 | Total imp 0.15 | Total imp 0.15 |
| 4 | Bel Acid 0.04 | Bel Acid 0.07 | Bel Acid 0.04 | Bel Acid 0.03 |
| | Bel Dimer 0.08 | Bel Dimer 0.13 | Bel Dimer 0.12 | Bel Dimer 0.03 |
| | Total imp 0.18 | Total imp 0.27 | Total imp 0.23 | Total imp 0.12 |
| 12 | Bel Acid 0.05 | Bel Acid 0.09 | Bel Acid 0.07 | Bel Acid 0.04 |
| | Bel Dimer 0.15 | Bel Dimer 0.18 | Bel Dimer 0.22 | Bel Dimer 0.04 |
| | Total imp 0.38 | Total imp 0.48 | Total imp 0.50 | Total imp 0.26 |
| 24 | Bel Acid 0.07 | Bel Acid 0.17 | Bel Acid 0.12 | Bel Acid 0.04 |
| | Bel Dimer 0.25 | Bel Dimer 0.28 | Bel Dimer 0.44 | Bel Dimer 0.06 |
| | Total imp 0.47 | Total imp 0.65 | Total imp 0.73 | Total imp 0.31 |

These results show that belinostat ASDs with polymers of the polyvinyl lactam class exhibit an outstanding chemical and physical stability even in long storage conditions with also no crystallization observed when analyzed by XRPD.

Example 6: In Vivo Performance in Dog (PK Profile)

Bioavailability of 3 spray dried dispersions (ASDs) was evaluated in a preclinical Dog PK study. The following formulations, 25% Belinostat in HPMCAS-M, PVPVA64 and PVPK30, were administered by oral gavage to 4 male Beagle dogs (7.0-9.0 Kg) in fasted state at a fixed dose of 50 mg per dog (equivalent to ~6.25 mg/kg). Animals were dosed once with each formulation with at least one week washout period between each dosing.

Blood samples were taken into heparinized tubes after each dose at the following time points: Predose, 5, 15 and 30 min, 1, 1.5, 2, 4, 6, 8, 12 and 24 hours from the jugular veins. Belinostat plasma concentrations were measured using a validated bioanalytical method (solid phase extraction, UHPLC-MS/MS, concentration range: 1-1000 ng/mL).

The aim of the study was to evaluate if the gain in solubility observed on in vitro dissolution provide increase of bioavailability compared to the crystalline form. Results are illustrated in FIG. 1.

IV dosing was performed for absolute bioavailability calculation and two controls groups were added: crystalline drug in capsule as a reference for low soluble formulation and an oral solution (IV formulation with L-arginine) as a reference for best achievable exposure with no solubility limitation. It is important to note that due to high pH (above pH 9.0) this oral solution is not pharmaceutically acceptable for clinical use.

Belinostat solutions, for IV and oral dose, were prepared at 50 mg/mL belinostat in 100 mg/mL L-arginine solution in water. Crystalline belinostat in capsule was prepared by manual weight filling of 50 mg belinostat (non-micronized) in size 2 hard gelatin capsule. Belinostat ASDs were administered as suspensions at 40 mg/mL in 0.5% Methocel in water vehicle.

Pharmacokinetic parameters were derived from the individual plasma concentration data by non-compartmental analysis using Phoenix WinNonlin (version 6.4).

$C_{max}$, $AUC_{0-12h}$ and bioavailability (F %), calculated for each dog and then averaged for the test population, are reported in the Table 4.

TABLE 4

Pharmacokinetic parameters of amorphous spray dried dispersion of belinostat in dogs.

| Formulations | Actual Dose range (mg/dog) | Mean $C_{max}$ (ng/mL) | Mean $AUC_{0-12h}$ (h*ng/mL) | Mean Bio-availability |
|---|---|---|---|---|
| IV | 42.2-45.9 | 4210 ($C_0$ 7109) | 1788 | — |
| Belinostat in capsules | 50.0-50.1 | 54 | 154 | 7% |
| Oral solution (with L-arginine) | 52.0-53.3 | 702 | 562 | 26% |
| Spray dried dispersion PVP VA64 | 54.3-56.1 | 409 | 433 | 19% |
| Spray dried dispersion HPMCAS-M | 43.9-45.3 | 338 | 443 | 25% |
| Spray dried dispersion PVP K30 | 55.3-59.2 | 1053 | 653 | 28% |

The oral solution is not suitable for oral administration.

The HPMCAS-M formulation is not suitable either as it is not chemically stable.

For the capsule containing crystalline belinostat, the observed average $AUC_{(0-12h)}$ was 154 ng×hr/mL. For the suspension containing the belinostat/PVPK30 dispersion, the average AUC was 4.2 times higher at 653 ng×hr/ml.

This example demonstrates that dosing a spray dried dispersion of belinostat/PVPK30 to dogs results in a higher systemic belinostat exposure than observed after dosing crystalline belinostat.

Such amorphous solid dispersion formulations of belinostat with improved pharmacokinetic properties were not heretofore known.

The invention claimed is:

1. An amorphous solid dispersion of belinostat comprising:
    a) Belinostat or a pharmaceutically acceptable salt, solvate or ester thereof;
    b) At least one polyvinyl lactam polymer; and
    c) Optionally, at least one additive.

2. The amorphous solid dispersion of belinostat according to claim 1, wherein said polyvinyl lactam polymer is chosen from chain polymers and copolymers comprising the following sub-unit:

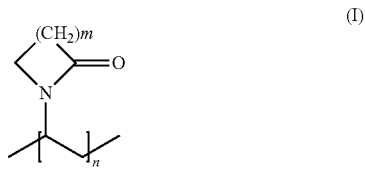

(I)

Wherein m is an integer chosen from 1, 2, 3 or 4 (β-, γ-, δ- or ε-lactam) and n represents the number of lactam repeating units in said sub-unit.

3. The amorphous solid dispersion of belinostat according to claim 1, wherein said polyvinyl lactam polymer is water soluble.

4. The amorphous solid dispersion of belinostat according to claim 1, wherein said polyvinyl lactam polymer is chosen from the group consisting of polyvinylpyrrolidone (PVP "Povidone"), PVP-polyvinyl acetate (Copovidone) and polyvinyl caprolactam-polyvinyl acetate-polyethylene glycol graft copolymer (PCL-PVAc-PEG).

5. The amorphous solid dispersion of belinostat according to claim 1, wherein said polyvinyl lactam polymer is chosen from PVP K30, PVP K12, PVP K25, PVP K90, PVP VA64 and the mixtures thereof.

6. The amorphous solid dispersion of belinostat according to claim 1, wherein it comprises:
    a) About 5 to 80% of belinostat (percentage weight); and
    b) About 20 to 95% of said polyvinyl lactam polymer (percentage weight).

7. The amorphous solid dispersion of belinostat according to claim 1, wherein said additive is chosen from the group consisting of: pH modifiers, antioxidants, dispersing agents, solubilizers, stabilizers, disintegrants or any mixture thereof.

8. The amorphous solid dispersion of belinostat according to claim 1, wherein said additive is histidine.

9. The amorphous solid dispersion of belinostat according to claim 1, wherein said dispersion comprises:
    Less than 0.2% of belinostat acid and/or belinostat dimer, upon release testing; and/or
    Less than 2% of belinostat acid and/or belinostat dimer upon storage for at least 18 months.

10. The process of preparation of the amorphous solid dispersion of belinostat according to claim 1 comprising the steps of:
    Preparing a solution of belinostat with said polyvinyl lactam polymer in a solvent;
    Spray-drying said solution.

11. A pharmaceutical composition comprising the amorphous solid dispersion of belinostat according to claim 1, and one or more pharmaceutically acceptable excipients.

* * * * *